United States Patent [19]

Micetich et al.

[11] Patent Number: 4,529,592
[45] Date of Patent: Jul. 16, 1985

[54] PENICILLIN DERIVATIVES

[75] Inventors: Ronald G. Micetich, Sherwood Park, Canada; Shigeru Yamabe, Kobe, Japan; Tomio Yamazaki; Naobumi Ishida, both of Tokushima, Japan; Takeshi Ishizawa, Naruto, Japan

[73] Assignee: Taiho Pharmaceutical Company, Limited, Tokyo, Japan

[21] Appl. No.: 501,560

[22] Filed: Jun. 6, 1983

[30] Foreign Application Priority Data

Jun. 21, 1982 [JP]   Japan .................. 57-107171

[51] Int. Cl.³ ............... C07D 499/00; A61K 31/425
[52] U.S. Cl. ............... 424/114; 260/245.2 R; 514/63; 514/192
[58] Field of Search ........ 260/245.2 T, 245.2 R; 424/270, 271, 114

[56] References Cited

U.S. PATENT DOCUMENTS 4,331,677  5/1982  Fogler et al. ............... 260/245.2 R

*Primary Examiner*—Nicholas S. Rizzo
*Attorney, Agent, or Firm*—Murray, Whisenhunt and Ferguson

[57] ABSTRACT

A penicillin derivative represented by the following formula

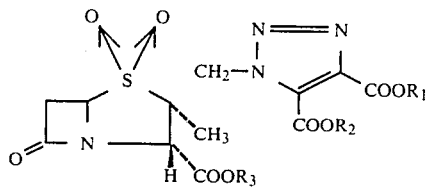

wherein $R_1$ and $R_2$ are each the same or different and represent hydrogen, $C_{1-18}$ alkyl, mononitro-substituted benzyl or group for forming a pharmaceutically acceptable salt and $R_3$ is selected from the group consisting of hydrogen, $C_{1-6}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt.

17 Claims, No Drawings

PENICILLIN DERIVATIVES

This invention relates to penicillin derivatives and to a process for preparing them.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve satisfactory effects against some types of microorganisms because of resistance of the microorganism to the β-lactam type antibiotics. The resistance thereof are usually attributable to β-lactamase produced by the microorganism. The β-lactamase is an enzyme which acts to cleave the β-lactam ring of the β-lactam type antibiotic, thereby causing the antibiotic to lose its antimicrobial activity. For this reason, the action of β-lactamase must be eliminated or inhibited so as to enable the β-lactam type antibiotic to produce satisfactory effects. The elimination or inhibition of the β-lactamase activity can be achieved by β-lactamase inhibitors, which are used conjointly with the β-lactam type antibiotic to increase the antimicrobial activity of the antibiotic.

It is an object of the present invention to provide novel compounds having β-lactamase inhibitory action.

It is another object of the invention to provide processes for preparing the same.

It is a further object of the invention to provide a pharmaceutical composition having excellent β-lactamase inhibitory action.

It is an additional object of the invention to provide compositions which, when combined with β-lactam type antibiotics, can increase the antibacterial activity of the antibiotics.

The penicillin derivatives of the present invention are represented by the formula

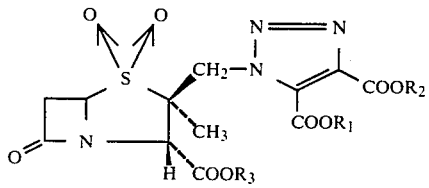

wherein $R_1$ and $R_2$ are each the same or different and represent hydrogen, $C_{1-18}$ alkyl, mononitro-substituted benzyl or group for forming a pharmaceutically acceptable salt and $R_3$ is selected from the group consisting of hydrogen, $C_{1-6}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt.

The penicillin derivatives of the present invention are all novel compounds and have β-lactamase inhibitory properties, hence useful as β-lactamase inhibitory agents.

The penicillin derivatives of the invention, when used in combination with a known β-lactam type antibiotic, can increase the antimicrobial activity of the β-lactam type antibiotic.

Examples of antibiotics which can be used conjointly with the compounds of the present invention are β-lactam antibiotics which exhibit antibacterial action against gram-positive or gram-negative bacteria and which include commonly used penicillins such as ampicillin, amoxicillin, hetacillin, ciclacillin, mecillinam, carbenicillin, sulbenicillin, ticarcillin, piperacillin, apalcillin, methicillin, mezlocillin and salts thereof; esters of penicillins such as bacampicillin, carindacillin, talampicillin, carfecillin and pivmecillinam; cephalosporins such as cepaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, ceforxadine, cefatrizine, cefadroxil, cephaloglycin, and salts thereof. The β-lactam antibiotics are usually used in an amount of about 0.1 to about 10 parts by weight, preferably about 0.2 to about 5 parts by weight, per part by weight of the compound of the invention.

Examples of the groups represented by $R_1$ and $R_2$ in the formula (I) include; $C_{1-18}$ alkyl such as methyl, ethyl, isopropyl, butyl, tert-butyl, pentyl, hexyl, decyl, undecyl, dodecyl, tetradecyl, hexadecyl, octadecyl and like straight- or branched-chain alkyl; and mononitro-substituted benzyl such as o-nitrobenzyl, p-nitrobenzyl and the like.

Examples of the groups represented by $R_3$ in the formula (I) include; $C_{1-6}$ alkyl such as methyl, ethyl, propyl, isopropyl, tert-butyl, pentyl, hexyl and like straight- or branched-chain alkyl; $C_{2-7}$ alkoxymethyl such as methoxymethyl, ethoxymethyl, propyloxymethyl, isopropyloxymethyl, butoxymethyl and hexyloxymethyl; $C_{3-8}$ alkylcarbonyloxymethyl such as methylcarbonyloxymethyl, ethylcarbonyloxymethyl, butylcarbonyloxymethyl and hexylcarbonyloxymethyl; $C_{4-9}$ alkylcarbonyloxyethyl such as methylcarbonyloxyethyl, ethylcarbonyloxyethyl, butylcarbonyloxyethyl and pivaloyloxyethyl; ($C_{5-7}$ cycloalkyl)carbonyloxymethyl such as cyclopentylcarbonyloxymethyl, cyclohexylcarbonyloxymethyl and cycloheptylcarbonyloxymethyl; $C_{9-14}$ benzylcarbonyloxyalkyl such as benzylcarbonyloxymethyl, benzylcarbonyloxyethyl, benzylcarbonyloxypropyl and benzylcarbonyloxybutyl; $C_{3-8}$ alkoxycarbonylmethyl such as methoxycarbonylmethyl, ethoxycarbonylmethyl, propyloxycarbonylmethyl and hexyloxycarbonylmethyl; $C_{4-9}$ alkoxycarbonylethyl such as methoxycarbonylethyl, ethoxycarbonylethyl, propyloxycarbonylethyl, butoxycarbonylethyl and hexyloxycarbonylethyl; halogenated $C_{1-6}$ alkyl substituted with 1 to 3 halogen atoms such as chloromethyl, 2,2-dibromoethyl and trichloroethyl; $C_{1-6}$ alkoxy- or nitro-substituted or unsubstituted benzyl such as p-methoxybenzyl, p-ethoxybenzyl, o-nitrobenzyl and p-nitrobenzyl; (5-substituted $C_{1-6}$ alkyl or phenyl or unsubstituted-2-oxo-1,3-dioxoden-4-yl)methyl such as (2-oxo-1,3-dioxoden-4-yl)methyl, (5-methyl-2-oxo-1,3-dioxoden-4-yl)methyl and (5-phenyl-2-oxo-1,3-dioxoden-4-yl)methyl; $C_{8-13}$ benzoyloxyalkyl such as benzoyloxymethyl, benzoyloxyethyl, benzoyloxypropyl and benzoyloxybutyl; etc. The ester residues represented by $R_3$ in the formula (I) include both carboxyl-protecting groups acceptable in the synthesis of penicillin compounds and pharmaceutically acceptable ester residues. A pharmaceutically acceptable ester having such residue is an ester which is easily hydrolyzed in vivo and which is a non-poisonous ester capable of rapidly decomposing in the blood or tissue of humans, thereby producing the corresponding acid of the formula (I) in which $R_3$ is hydrogen atom. Generally in the synthesis of penicillin compounds, ester-protecting groups are used in the art to protect penicillin carboxyl groups or other carboxyl groups. While it is difficult to determine which ester-protecting group should be used, considerations is usually given to select esters in which the protecting group per se is sufficiently stable in the reaction and which does not permit cleavage of the β-lactam ring in removal of the ester-protecting groups. Most commonly used as such ester-protecting groups are p-nitrobenzyl group, benzhydryl group, trichloroethyl group, trichlorosilyl group, tetrahydropyranyl group, etc. Examples of the pharmaceutically acceptable ester groups are phthalidyl, crotonolacton-4-yl, γ-butyrolactan-4-yl, (2-oxo-1,3-dioxoden-4-yl)methyl, etc.

Examples of the group for forming a pharmaceutically acceptable salt represented by $R_1$, $R_2$ and $R_3$ in the formula (I) include; sodium, potassium, lithium, or like alkali metal atoms; calcium, magnesium or like alkaline earth metal atoms; cyclohexylamine, trimethylamine, diethanolamine or like the organic amine residues; alginine, lysine or like basic amino acid residues; ammonium residues, etc.

The penicillin derivatives of the present invention having the formula (I) can be prepared according to the reaction equation given below.

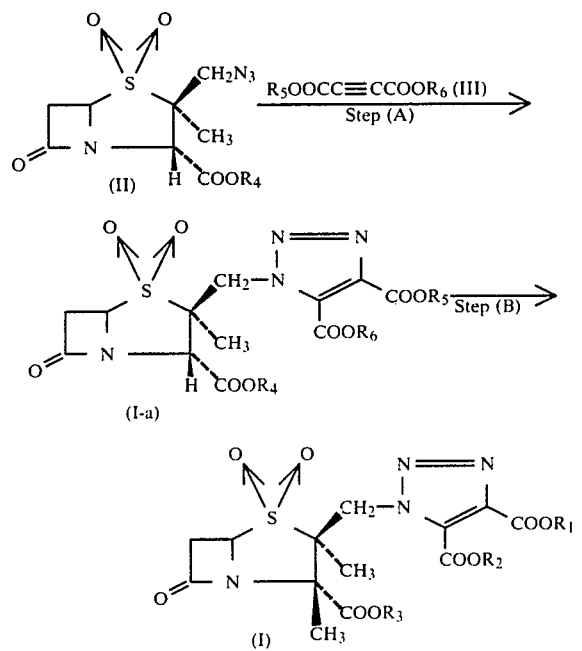

In the foregoing formulae, $R_1$, $R_2$ and $R_3$ are as defined above, $R_4$ represents penicillin carboxyl-protecting group and $R_5$ and $R_6$ represent hydrogen, $C_{1-8}$ alkyl or mononitro-substituted benzyl.

Examples of the penicillin carboxyl protecting group expressed by $R_4$ include known groups such as those described in Japanese Unexamined Patent Publication No. 81380/1974 and H. E. Flynn, "Cephalosporins and Penicillins, Chemistry and Biology" (published in 1972 by Academic Press). Specific examples thereof are ethyl, propyl, tert-butyl, trichloroethyl and like substituted or unsubstituted alkyl groups; benzyl, diphenyl methyl, p-nitrobenzyl and like substituted or unsubstituted aralkyl groups; acetoxymethyl, benzyloxymethyl and like acyloxyalkyl groups, methoxymethyl and like alkoxyalkyl groups; and other groups such as tetrahydropyranyl, dimethylaminoethyl, dimethyldichlorosilyl, trichlorosilyl and like groups.

The steps (A) and (B) of the foregoing process will be described below in detail.

Step (A)

A penicillanic acid derivative of the formula (II) is reacted with an acetylene derivative of the formula (III) to provide a compound of the formula (I-a). The reaction is conducted in a suitable solvent by reacting a known penicillanic acid derivative of the formula (II) with a known acetylene derivative of the formula (III) in an amount of about 1 to about 50 moles, preferably about 1 to about 10 moles, per mole of the derivative of the formula (II).

The solvents useful in the reaction are not particularly limited and include any of those which do not adversely affect the reaction. Specific examples of the solvents are benzene, toluene, xylene and like aromatic hydrocarbons, acetone and like polar organic solvents; etc. These solvents are used singly or in mixture. The reaction proceeds usually at a temperature of between about 50° C. and a boiling point of the solvent or at a temperature of less than 200° C. in a sealed reactor, and goes to completion in about 2 to about 72 hours.

Depending upon the kind of the penicillin carboxyl-protecting group represented by $R_4$, the compounds of the formula (I-a) obtained in step (A) may be esters of the penicillin derivatives of the present invention having the formula (I). The compounds of the formula (I-a) are preferably subjected to de-esterification to form a derivative of the formula (I) in the form of free acid which, in turn, is converted into a pharmaceutically acceptable salt or ester thereof as in the following step (B). The compound of the formula (I-a) can also be made into an ester of the formula (I) by the conventional ester interchange reaction in the step (B).

Step (B)

The compound of the formula (I-a) is subjected to de-esterification without or after isolation from the reaction mixture obtained in step (A), whereby a penicillin derivative of the formula (I) is obtained in the form of free acid.

As the de-esterification method, reduction, hydrolysis, treatment with an acid and like method can be employed for converting the carboxyl-protecting group to carboxyl group. For example, if the carboxyl-protecting group is an active ester, the reaction frequently proceeds with ease under mild hydrolysis conditions or by merely bringing the ester into contact with water. The reduction method is employed when the carboxyl-protecting group is trichloroethylbenzyl, p-nitrobenzyl, diphenyl methyl or the like. Treatment with an acid is adopted when the carboxyl-protecting group is 4-methoxybenzyl, tert-butyl, trityl, diphenylmethyl, methoxymethyl, tetrahydropyranyl or the like.

The reduction can be conducted by treating the ester of the formula (I-a) with a mixture of (a) zinc, zinc-amalgam or like metal and/or chromium chloride, chromium acetate or like chromium salt and (b) formic acid, acetic acid or like acid. Alternatively, the reduction can be conducted with use of a catalyst in hydrogen atmosphere in a solvent. Examples of the catalysts are platinum, platinum oxide, palladium, palladium oxide, palladium-barium sulfate, palladium-calcium carbonate, palladium-carbon, nickel oxide, Raney-nickel, etc. The solvents are not particularly limited so far as they do not adversely affect the reaction, and include methanol, ethanol and like alcohols; tetrahydrofuran, dioxane and like ethers; ethyl acetate and like esters; acetic acid and like fatty acids; and a mixture of these organic solvents and water.

The acids useful for eliminating the carboxyl-protecting group of the ester of the formula (I-a) are formic acid, acetic acid and like lower fatty acids; trichloroacetic acid, trifluoroacetic acid and like trihalogenated acetic acids; hydrochloric acid, hydrofluoric acid and like hydrohalogenic acids; p-toluene-sulfonic acid, trifluoromethane-sulfonic acid and like organic sulfonic acids; and a mixture of these. In this reaction, when the acid used is in a liquid state and acts also as a solvent, it is not necessary to use other solvents. However, dimethylformamide, dichloromethane, chloroform, tetrahydrofuran, acetone and like solvents which do not adversely affect the reaction may be used.

The penicillin derivative of the present invention having the formula (I) in the form of free acid can be transformed by the salt-forming reaction or esterification commonly employed in the art into a pharmaceutically acceptable salt or ester as contemplated.

If the ester residue is, for example, 3-phthalidyl, crotonolacton-4-yl, γ-butyrolacton-4-yl or like group, the penicillin derivative of the formula (I-a) can be alkylated by using 3-halogenated phthalide, 4-halogenated crotonolactone, 4-halogenated-butyrolactone or the like. Suitable halogens of the foregoing halides include chlorine, bromine, iodine, etc. The reaction is carried out by dissolving the salt of the penicillin derivative of the formula (I-a) in N,N-dimethylformamide or like suitable polar organic solvent and adding an approximately equimolecular amount of a halide to the solution. The reaction temperature ranges from about 0° to about 100° C., preferably from about 15° to about 35° C. Suitable salts of the penicillin derivative to be used in the esterification are salts of sodium, potassium or like alkali metals; salts of triethylamine, ethyldiisopropylamine, N-ethylpiperidine, N,N-dimethylaniline, N-methylmorpholine or like tertiary amines, etc. After completion of the reaction, the contemplated product can be easily separated by the conventional method and also can be purified, when required, by recrystallization, thin layer chromatography, column chromatography or like method.

The compound of the formula (II) to be used as the starting material in the step (A) is a novel compound undisclosed in literature and can be synthesized by the method described in Japanese patent application No. 69142/1982 (relating to an invention accomplished by us). The disclosed method comprises the steps of reacting a metal azide with a known derivative of penicillanic acid of the formula

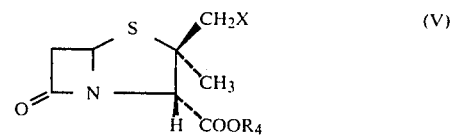

wherein X represents chlorine atom or bromine atom and $R_4$ represents penicillin carboxyl-protecting group, oxydizing the reaction mixture and subjecting the resulting compound to de-esterification.

The foregoing method will be described below in detail. The reaction between the compound of the formula (V) and the metal azide is conducted in a suitable solvent by using the metal azide in an amount of about 1 to about 50 moles, preferably about 1 to about 10 moles, per mole of the compound of the formula (V). Examples of the metal azides which can be used include those commonly used, such as sodium azide, potassium azide and like azides of alkali metals, and barium azides and like azides of alkaline earth metals. Useful solvents are not particularly limited as far as they do not adversely affect the reaction. Examples of useful solvents are dimethylformamide, ethyl acetate, acetone, dichloromethane, tetrahydrofuran, dioxane, methanol, ethanol and like organic solvents. These organic solvents can be used singly or in mixtures. Also a mixture of such solvent and water is usable. The reaction proceeds at a temperature of usually about −20° to about 100° C., preferably about 0° to about 100° C. The resulting product can be used in subsequent oxidation without isolation, or alternatively after isolation and purification by a conventional method. The oxidation subsequent to the azide-forming reaction is conducted by using an oxidizing agent commonly employed such as permanganic acid, periodic acid, peracetic acid, performic acid, trifluoroperacetic acid, perbenzoic acid, m-chloroperbenzoic acid, hydrogen peroxide, etc. The oxidizing agent can be used in large excess, and may be employed preferably in an amount of about 1 to about 2 moles per mole of the starting compound. The oxidation is carried out usually in a suitable solvent. Useful solvents include any of those which do not adversely affect the oxidation reaction such as chloroform, pylridine, tetrahydrofuran, dioxane, methylene chloride, carbon tetrachloride, acetic acid, formic acid, dimethylformamide, water, etc. The oxidation is performed at a temperature which is not particularly limited but generally ranges from room temperature to cooling temperature, preferably about 0° to about 30° C.

The compound thus obtained is subjected to de-esterification whereby the compound of the formula (II) can be produced. The de-esterification is effected under the same conditions as shown in the reaction scheme of the step (B). The process for preparing the compound of the formula (II) is described in detail in reference examples to be set forth later.

The penicillin derivative of the present invention is mixed with a suitable antibiotic substance to form a preparation which is orally or parenterally administered. Alternatively, the present compound and a suitable antibiotic can be separately administered. Thus the derivatives of the formula (I) can be used for treating infectious disease of human beings and other animals.

The composition of the present invention may be made into tablets, pills, capsules, granules, powders, syrups, lozenges, solutions, suspensions, etc. for oral administration and aqueous, suspending or water-soluble preparations for intravenous, subcutaneous or intramuscular injections.

Carriers useful in formulating the preparations are those commonly used pharmaceutically acceptable non-toxic carriers such as gelatin, lactose, starch, magnesium stearate, talc, vegetable oil, animal oil, polyalkylene glycol, etc. The carrier may be used with other additives such as diluents, binders, buffer agents, preservatives, glazes, disintegrators, coating agents, etc.

The daily dose of the preparation can be appropriately determined and is not particularly limited. Preferably the daily dose is such that the total amount of the present compound and β-lactam antibiotic is about 1 to about 200 mg/Kg body weight for oral administration and about 1 to about 100 mg/Kg body weight for parenteral administration.

The present invention will be described below in more detail with reference to examples given below.

REFERENCE EXAMPLE 1

Preparation of benzhydryl 2β-azidomethyl-2α-methylpenam-3α-carboxylate

An aqueous solution of 5.00 g of sodium azide and 53 ml of water was added to a solution of benzhydryl 2β-chloromethyl-2α-methylpenam-3α-carboxylate (5.13 g) in dimethylformamide (155 ml). The mixture was stirred at room temperature for 4 hours. The resulting reaction mixture was poured into cooled water and the mixture was extracted with ethyl acetate. The ethyl acetate layer was washed with water, dried over magnesium sulfate and concentrated to provide 4.87 g of the contemplated product as oil in 93% yield.

Infrared absorption spectrum (nujol): $\nu$ max (cm$^{-1}$): 2120, 1812, 1765.

Nuclear magnetic resonance spectrum (CDCl$_3$): $\delta$(ppm): 1.30 (3H, s), 3.25 (2H, m), 3.42 (1H, d), 3.63 (1H, d), 4.75 (1H, s), 4.76 (1H, m), 7.00 (1H, s), 7.40 (10H, s).

REFERENCE EXAMPLE 2

Preparation of benzhydryl 2β-azidomethyl-2α-methylpenam-3α-carboxylate-1,1-dioxide A 7.03 g quantity of benzhydryl 2β-azidomethyl-2α-methylpenam-3α-carboxylate was dissolved in 40 ml of water and 240 ml of of acetic acid. To the solution was added 6.02 g of potassium permanganate over a period of more than 1 hour. The mixture was stirred at room temperature for 2.5 hours. Iced water was added to the reaction mixture to form a precipitate which was filtered off and washed with water. The resulting solids were dissolved in ethyl acetate and the solution was washed with an aqueous solution of sodium hydrogencarbonate, dried over magnesium sulfate and concentrated, giving 5.48 g of the contemplated compound in 72% yield.

Infrared absorption spectrum (nujol): $\nu$ max (cm$^{-1}$): 2120, 1812, 1765.

Nuclear magnetic resonance spectrum (CDCl): $\delta$ (ppm): 1.18 (3H, s), 3.50 (2H, d), 3.72 (1H, d), 3.93 (1H, d), 4.60 (1H, m), 4.65 (1H, s), 7.00 (1H, s), 7.36 (10H, s).

REFERENCE EXAMPLE 3

Preparation of p-nitrobenzyl 2β-azidomethyl-2α-methylpenam-3α-carboxylate

The procedure of Reference Example 1 was repeated with the exception of using as the starting material p-nitrobenzyl 2β-chloromethyl-2α-methylpenam-3α-carboxylate, affording the above contemplated compound.

Infrared absorption spectrum (KBr): $\nu$ max (cm$^{-1}$): 2120, 1798, 1760.

Nuclear magnetic resonance spectrum (CDCl$_3$): $\delta$ (ppm): 1.40 (3H, s), 3.12 (1H, dd), 3.50 (2H, s), 3.62 (1H, dd), 4.83 (1H, s), 5.29 (2H, s), 5.36 (1H, dd), 7.56 (2H, d), 8.26 (2H, d).

REFERENCE EXAMPLE 4

Preparation of p-nitrobenzyl 2β-azidomethyl-2α-methylpenam-3α-carboxylate-1,1-dioxide The procedure of Reference Example 2 was followed with the exception of using as the starting material p-nitrobenzyl 2β-azidomethyl-2α-methylpenam-3α-carboxylate, giving the above contemplated compound.

Infrared absorption spectrum (KBr): $\nu$ max (cm$^{-1}$): 2120, 1770.

Nuclear magnetic resonance spectrum (CDCl$_3$): $\delta$ (ppm): 1.42 (3H, s), 3.45–3.60 (2H, m), 3.75 (1H, d), 3.96 (1H, d), 4.56–4.75 (1H, m), 4.64 (1H, s), 5.33 (2H, s), 7.56 (2H, d), 8.26 (2H, d).

EXAMPLE 1

Preparation of benzhydryl 2β-(4,5-dimethoxy-carbonyl-1,2,3-triazol-1-yl)methyl-2α-methylpenam-3α-carboxylate-1,1-dioxide (Compound 1)

A mixture of 0.870 g of benzhydryl 2β-azidomethyl-2α-methylpenam-3α-carboxylate-1,1-dioxide and 0.618 g of dimethylacetylene-dicarboxylate was stirred in 15 ml of benzene with reflux in nitrogen atmosphere for 18 hours. The solvent was removed by distillation. The residue was chromatographed on silica gel column with ethyl acetate-chloroform (1:3) as elutate, giving 0.495 g of the contemplated product as light yellow crystals in 44% yield which melts at 75° to 77° C.

Infrared absorption spectrum (KBr): $\nu$ max (cm$^{-1}$): 1800, 1735.

Nuclear magnetic resonance spectrum (CDCl$_2$): $\delta$ (ppm): 1.20 (3H, s), 3.48 (2H, t), 3.97 (3H, s), 3.98 (3H, s), 4.59 (1H, m), 4.95 (1H, s), 5.26 (2H, s), 6.97 (1H, s), 7.36 (10H, s).

EXAMPLE 2

Preparation of sodium 2β-(4,5-dimethoxycarbonyl-1,2,3-triazol-1-yl)methyl-2α-methylpenam-3α-carboxylate-1,1-dioxide (Compound 2)

Hydrogenation was conducted at ordinary pressure and room temperature by using 100 ml of tetrahydrofuran, 100 ml of water, 116 mg of benzhydryl 2β-(4,5-dimethoxycarbonyl-1,2,3-triazol-1-yl)-methyl-2α-methylpenam-3α-carboxylate-1,1-dioxide, 58 mg of 10% palladium charcoal and 17 mg of sodium bicarbonate. After the absorption of the hydrogen was completed, the reaction mixture was filtered and the tetrahydrofuran was removed from the filtrate at reduced pressure by distillation. The residue was washed with chloroform and the aqueous solution was concentrated at reduced pressure. The aqueous mixture was washed with chloroform and was chromatographed with a column of high porous polymer and eluted with water-10% acetone in water (gradient). The liquid thus obtained was freeze-dried to obtain 53 mg of the contemplated product as white powder in 60% yield. The white powder decomposed at over 165° C.

Infrared absorption spectrum (KBr): $\nu$ max (cm$^{-1}$): 1785, 1735, 1630.

Nuclear magnetic resonance spectrum (D$_2$O): $\delta$ (ppm): 1.41 (3H, s), 3.40 (1H, dd), 3.80 (1H, dd), 3.98 (3H, s), 4.05 (3H, s), 4.51 (1H, s), 5.03 (1H, dd), 5.48 (2H, d).

EXAMPLE 3

Preparation of p-nitrobenzyl 2$\beta$-(4,5-diethoxycarbonyl-1,2,3-triazol-1-yl)methyl-2$\alpha$-methylpenam-3$\alpha$-carboxylate-1,1-dioxide (Compound 3)

The same procedure as in Example 1 was repeated with the exception of using as the starting material p-nitrobenzyl 2$\beta$-azidomethyl-2$\alpha$-methylpenam-3$\alpha$-carboxylate-1,1-dioxide, producing the above product.

Infrared absorption spectrum (KBr): $\nu$ max (cm$^{-1}$): 1805, 1735.

Nuclear magnetic resonance spectrum (CDCl$_3$): $\delta$ (ppm): 1.33–1.48 (9H, m), 3.30–3.72 (2H, m), 4.42 (2H, q), 4.45 (2H, q), 4.64–4.71 (1H, m), 5.02 (1H, s), 5.22–5.40 (4H, m), 7.55 (2H, d), 8.24 (2H, d).

EXAMPLE 4

Preparation of 2$\beta$-(4,5-diethoxycarbonyl-1,2,3-triazol-1-yl)methyl-2$\alpha$-methylpenam-3$\alpha$-carboxylic acid-1,1-dioxide (Compound 4) and sodium salt thereof (Compound 5)

A 3.5 g quantity of p-nitrobenzyl 2$\beta$-(4,5-diethoxycarbonyl-1,2,3-triazol-1-yl)methyl-2$\alpha$-methylpenam-3$\alpha$-carboxylate-1,1-dioxide was hydrogenated at an initial pressure of 3 atm. by using 1.1 g of sodium hydrogencarbonate and 0.6 g of 10% palladium charcoal in 90 ml of ethyl acetate and 90 ml of water. In one hour, the reaction mixture was sedimented and the aqueous layer was separated. The aqueous layer was washed twice with ether and its pH was adjusted to 1.7 with diluted hydrochloric acid. The aqueous solution was extracted with ethyl acetate and dried over magnesium sulfate. The solvent was removed at reduced pressure by distillation, whereby 2.2 g of 2$\beta$-(4,5-diethoxycarbonyl-1,2,3-triazol-1-yl)methyl-2$\alpha$-methylpenam-3$\alpha$-carboxylic acid in the form of amorphous crystals in 83% yield.

A 170 mg quantity of 2$\beta$-(4,5-diethoxycarbonyl-1,2,3-triazol-1-yl)methyl-2$\alpha$-methylpenam-3$\alpha$-carboxylic acid was dissolved in a solution of 84 mg g of sodium hydrogencarbonate in 10 ml of water. The resulting solution was purified with an MCI gel (product of Mitsubishi Kasei Co., Ltd., Japan). The liquid thus obtained was freeze-dried, giving 130 mg of amorphous product in 73% yield which melts at 155° to 160° C. (decomposition).

Infrared absorption spectrum (KBr): $\nu$ max (cm$^{-1}$): 1785, 1735, 1630.

Nuclear magnetic resonance spectrum (D$_2$O): $\delta$ (ppm): 1.32–1.49 (9H, m), 3.34–3.82 (2H, m), 4.35–4.65 (5H, m), 5.01–5.07 (1H, m), 5.47 (2H, s), 5.03 (1H, dd), 5.48 (2H, d).

EXAMPLE 5

Preparation of 2$\beta$-(4,5-dimethoxycarbonyl-1,2,3-triazol-1-yl)methyl-2$\alpha$-methylpenam-3$\alpha$-carboxylic acid-1,1-dioxide (Compound 6)

Hydrogenation was carried out in 100 ml of tetrahydrofuran and 100 ml of water at room temperature by using 116 mg of benzhydryl 2$\beta$-(4,5-dimethoxycarbonyl-1,2,3-triazol-1-yl)methyl-2$\alpha$-methylpenam-3$\alpha$-carboxylate-1,1-dioxide, 58 mg of 10% palladium charcoal and 17 mg of sodium hydrogencarbonate. After completion of absorption of hydrogen, the reaction liquid was filtered and the tetrahydrofuran was distilled off from the filtrate at reduced pressure. The residue was washed with chloroform. After adjusting its pH to 1.5 to 1.7 with diluted hydrochloric acid, the aqueous solution was washed with chloroform, extracted with ethyl acetate and dried over magnesium sulfate. The ethyl acetate was distilled off at reduced pressure, and the residue was dissolved in water. The solution was freeze-dried to provide 83 mg of amorphous product in 76% yield which has a melting point of 135° to 145° C. (decomposition).

Infrared absorption spectrum (KBr) $\nu$ max (cm$^{-1}$): 1805, 1735.

Nuclear magnetic resonance spectrum (CDCl$_3$+DMSO-d$_6$): $\delta$ (ppm): 1.55 (3H, s), 3.2–3.6 (2H, m), 3.96 (3H, s), 4.02 (3H, s), 4.68 (1H, s), 4.6–4.8 (1H, m), 5.35 (2H, s).

EXAMPLE 6

Preparation of chloromethyl (2$\beta$-(4,5-dimethoxycarbonyl-1,2,3-triazol-1-yl)methyl-2$\alpha$-methylpenam-3$\alpha$-carboxylate-1,1-dioxide (Compound 7)

A 1.25 g quantity of sodium hydrogencarbonate and 0.133 g of tetrabutylammonium hydrogensulfate were added with stirring at less than 10° C. to 1.61 g of 2$\beta$-(4,5-dimethoxycarbonyl-1,2,3-triazol-1-yl)methyl-2$\alpha$-methylpenam-3$\alpha$-carboxylic acid-1,1-dioxide, 8 ml of dichloromethane and 8 ml of water. To the mixture was dropwise added at the same temperature 0.74 g of chloromethyl chlorosulfonate. The mixture was stirred at room temperature for 30 minutes. The organic layer was separated, washed once with water and dried over magnesium sulfate. The solvent was removed by distillation at reduced pressure to obtain as the residue 1.5 g of amorphous product in 83% yield.

Infrared absorption spectrum (KBr): $\nu$ max (cm$^{-1}$): 1805, 1735.

Nuclear magnetic resonance spectrum (CDCl$_3$): $\delta$ (ppm): 1.55 (3H, s), 3.2–3.8 (2H, m), 3.99 (3H, s), 4.03 (3H, s), 4.6–4.8 (1H, m), 5.01 (1H, s), 5.32 (2H, d), 5.62 (1H, d), 5.81 (1H, d).

EXAMPLE 7

Preparation of iodomethyl 2$\beta$-(4,5-dimethoxycarbonyl-1,2,3-triazol-1-yl)methyl-2$\alpha$-methylpenam-3$\alpha$-carboxylate-1,1-dioxide (Compound 8)

A 1.05 g quantity of chloromethyl 2$\beta$-(4,5-dimethoxycarbonyl-1,2,3-triazol-1-yl)methyl-2$\alpha$-methylpenam-3$\alpha$-carboxylate-1,1-dioxide, 0.52 g of sodium idodide and 1.8 ml of acetone were stirred at room temperature for 18 hours. To the reaction mixture was added 1.5 ml of water and the resulting mixture was adjusted to a pH of 7 to 8 with an aqueous solution of sodium hydrogencarbonate. Thereto was added 1.5 ml of water and the mixture was decolorized with an aqueous solution of 0.5M sodium thiosulfate. The mixture was extracted with dicloromethane, washed with water and dried over magnesium sulfate. The solvent was distilled off at reduced pressure to produce 1.1 g of amorphous product in 78% yield.

Infrared absorption spectrum (KBr): $\nu$ max (cm$^{-1}$): 1800, 1730.

Nuclear magnetic resonance spectrum (CDCl$_3$): $\delta$ (ppm): 1.56 (3H, s), 3.2–3.8 (2H, m), 3.99 (3H, s), 4.03 (3H, s), 4.6–4.8 (1H, m), 4.97 (1H, s), 5.30 (2H, d), 5.85 (1H, d), 5.96 (1H, d).

EXAMPLE 8

Preparation of p-nitrobenzyl 2$\beta$-(4,5-dimethoxycarbonyl-1,2,3-triazol-1yl)methyl-2$\alpha$-methylpenam-3$\alpha$-carboxylate-1,1-dioxide (Compound 9)

A 3.5 g quantity of p-nitrobenzyl 2$\beta$-azidomethyl-2$\alpha$-methylpenam-3$\alpha$-carboxylate-1,1-dioxide and 4.8 g of dimethylacetylenedicarboxylate in 80 ml of absolute benzene were refluxed under nitrogen atmosphere for 18 hours. The solvent was distilled off at reduced pressure to provide 4.7 g of the contemplated compound.

Infrared absorption spectrum (KBr): $\nu$ max (cm$^{-1}$): 1805, 1735.

Nuclear magnetic resonance spectrum (CDCl$_3$): $\delta$ (ppm): 1.43 (3H, s), 3.2–3.4 (2H, m), 3.96 (3H, s), 3.99 (3H, s), 4.64–4.76 (1H, m), 4.98 (1H, s), 5.04–5.44 (4H, m), 7.56 (2H, d), 8.23 (2H, d).

EXAMPLE 9

Preparation of: p-nitrobenzyl 2$\beta$-(4,5-di-n-butoxycarbonyl-1,2,3-triazol-1yl)methyl-2$\alpha$-methylpenam-3$\alpha$-carboxylate-1,1-dioxide (Compund 10); p-nitrobenzyl 2$\beta$-(4,5-di-isobutoxycarbonyl-1,2,3-triazol-1-yl)methyl-2$\alpha$-methylpenam-3$\alpha$-carboxylate-1,1-dioxide (Compound 11); p-nitrobenzyl 2$\beta$-(4,5-di-n-tetradecyloxycarbonyl-1,2,3-triazol-1-yl)methyl-2$\alpha$-carboxylate-1,1-dioxide (Compound 12); p-nitrobenzyl 2$\beta$-(4,5-di-n-octadecyloxycarbonyl-1,2,3-triazol-1-yl)methyl-2$\alpha$-methylpenam-3$\alpha$-carboxylate-1,1-dioxide (Compound 13); p-nitrobenzyl 2$\beta$-[4,5-di-(p-nitrobenzyloxy)carbonyl-1,2,3-triazol-1-yl]methyl-2$\alpha$-methylpenam-3$\alpha$-carboxylate-1,1-dioxide (Compound 14).

The foregoing compounds were prepared in the same manner as in Example 1.

Compound 10

Infrared absorption spectrum (NaCl): $\nu$ max (cm$^{-1}$): 1805, 1730.

Nuclear magnetic resonance spectrum (CDCl$_3$): $\delta$ (ppm): 0.96 (6H, t), 1.43 (3H, s), 1.2–2.0 (8H, m), 3.3–3.7 (2H, m), 4.2–4.5 (4H, m), 4.6–4.7 (1H, m), 5.02 (1H, s), 5.0–5.4 (4H, m), 7.54 (2H, d), 8.24 (2H, d).

Compound 11

Infrared absorption spectrum (NaCl): $\nu$ max (cm$^{-1}$): 1805, 1735.

Nuclear magnetic resonance spectrum (CDCl$_3$) $\delta$ (ppm): 0.98 (6H, d), 1.00 (6H, d), 1.43 (3H, s), 1.8–2.3 (2H, m), 3.3–3.7 (2H, m), 4.15 (4H, d), 4.6–4.7 (1H, m), 5.02 (1H, s), 5.0–5.4 (4H, m), 7.55 (2H, d), 8.24 (2H, d).

Compound 12

Infrared absorption spectrum (KBr): $\nu$ max (cm$^{-1}$): 1800, 1730.

Nuclear magnetic resonance spectrum (CDCl$_3$): $\delta$ (ppm): 0.70–1.90 (57H m), 3.44–3.60 (2H, m), 4.22–4.45 (4H, m), 4.58–4.70 (1H, m), 5.03 (1H, s), 4.95–5.40 (4H, m), 7.54 (2H, d), 8.24 (2H, d).

Compound 13

Infrared absorption spectrum (KBr): $\nu$ max (cm$^{-1}$): 1800, 1730.

Nuclear magnetic resonance spectrum (CDCl$_3$) $\delta$ (ppm): 0.70–1.90 (73H m), 3.44–3.60 (2H, m), 4.22–4.45 (4H, m), 4.54–4.68 (1H, m), 5.03 (1H, s), 4.80–5.40 (4H, m), 7.53 (2H, d), 8.24 (2H, d).

Compound 14

Infrared absorption spectrum (KBr): $\nu$ max (cm$^{-1}$): 1800, 1735.

Nuclear magnetic resonance spectrum (CDCl$_3$): $\delta$ (ppm): 1.46 (3H, s), 3.42–3.56 (2H, m), 4.58–4.70 (1H, m), 4.88 (1H, s), 5.31 (4H, s), 5.46 (4H, s), 7.42–7.66 (6H, m), 8.05–8.30 (6H, m).

EXAMPLE 10

Preparation of tri-sodium 2$\beta$-(4,5-dicarboxy-1,2,3-triazol-1-yl)methyl-2$\alpha$-methylpenam-3$\alpha$-carboxylate-1,1-dioxide (Compound 15)

The above compound with a melting point of over 203° C. (decomposition) was produced in the same manner as in Example 9 from Compound 14.

Infrared absorption spectrum (KBr): $\nu$ max (cm$^{-1}$): 1780, 1720.

Nuclear magnetic resonance spectrum (D$_2$O): $\delta$ (ppm): 1.42 (3H, s), 3.25–3.82 (2H, m), 4.50 (1H, s), 4.95–5.04 (1H, m), 5.52 (2H, dd).

The compounds of the present invention obtained above were checked for pharmacological activity in the following manner.

(1) $\beta$-lactamase inhibitory activity

The compounds of the present invention obtained in the examples were tested by pH Stat method (Journal of Pharmaceutical Science, Vol. 61, No. 10, pp 1954 to 1958, published in 1972) for inhibitory activity against penicillinase ($\beta$-lactamase) from Bacillus SP.

The test results revealed that the Compound 2 had a 50%-$\beta$-lactamase inhibitory concentration (IC$_{50}$) of $3 \times 10^{-7}$M and Compound 15 had an IC$_{50}$ of $2.3 \times 10^{-6}$M. The other derivatives obtained in the other examples were found to have similar values in IC$_{50}$.

(2) Antibacterial activity (synergistic effects attainable by the combined use of the present compounds and ampicillin)

The compounds of the present invention and ampicillin, each singly used, were checked for minimal inhibitory concentration (MIC) against the bacteria listed in Table 1 given below in which the bacteria in the list were cultivated at 37° C. for 20 hours by the standard method of Japan Society of Chemotherapy (Chemotherapy, Vol. 29, No. 1 p 76 to 79). The MICs of ampicillin as combined with the present compounds (10 $\mu$g/ml) were also measured in the same manner against the same bacteria. Mueller Hinton Broth (Difco) was used as the growth medium and Mueller Hinton Agar (Difco) as the medium measuring the MIC. Table 1 below shows the results.

The bacterial used in the tests are those heretofore known and preserved in a depository, and are all offered by Dr. Nishino at Department of Microbiology, Kyoto College of Pharmacy except *P. vulgaris*.

TABLE 1

| | | MIC (μg/ml) | | |
|---|---|---|---|---|
| Test Bacteria | Amount of Innoculum size (cell/ml) | Ampicillin | Compound 2 | Combined use of Ampicillin and Compound 2 (10 μg/ml) |
| S. aureus S-54 | $10^7$ | 100 | >50 | 0.39 |
| S. aureus ATCC 90124 | $10^7$ | 50 | >50 | ≦0.2 |
| E. coli TH-13 | $10^7$ | 400 | >50 | 25 |
| E. coli TH-34 | $10^7$ | 800 | >50 | 50 |
| P. mirabilis 121-1 | $10^7$ | 800 | >50 | 1.56 |
| P. vulgaris IID OX-19 | $10^7$ | 25 | 25 | ≦0.2 |
| S. marcescens TH-05 | $10^7$ | 800 | >50 | 50 |

Given below are examples of preparation of the present antibacterial compositions.

PREPARATION EXAMPLE 1

| | |
|---|---|
| Ampicillin | 200 mg |
| Compound 2 | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

PREPARATION EXAMPLE 2

| | |
|---|---|
| Amoxycillin | 100 mg |
| Compound 5 | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

PREPARATION EXAMPLE 3

| | |
|---|---|
| Pivmecillinam | 70 mg |
| Compound 15 | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |
| Total | 220 mg |
| | (amount per tablet) |

The above ingredients are formulated in the proportions listed above into a tablet.

PREPARATION EXAMPLE 4

| | |
|---|---|
| Compound 5 | 120 mg |
| Hydroxypropyl cellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

We claim:

1. A penicillin derivative represented by the following formula

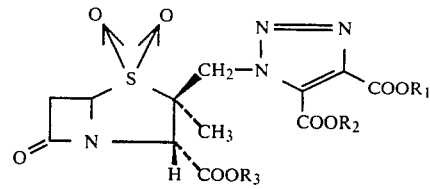

wherein $R_1$ and $R_2$ are each the same or different and represent hydrogen, $C_{1-18}$ alkyl, mononitro-substituted benzyl or group for forming a pharmaceutically acceptable salt and $R_3$ is selected from the group consisting of hydrogen, $C_{1-6}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt.

2. The penicillin derivative as defined in claim 1 wherein $R_3$ is $C_{2-7}$ alkoxymethyl.

3. The penicillin derivative as defined in claim 1 wherein $R_3$ is $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl or $C_{8-13}$ benzoyloxyalkyl.

4. The penicillin derivative as defined in claim 1 wherein $R_3$ is $C_{3-8}$ alkoxycarbonylmethyl or $C_{4-9}$ alkoxycarbonylethyl.

5. The penicillin derivative as defined in claim 1 wherein $R_3$ is phthalidyl.

6. The penicillin derivative as defined in claim 1 wherein $R_3$ is crotonolacton-4-yl and γ-butyrolacton-4-yl.

7. The penicillin derivative as defined in claim 1 wherein $R_3$ is (5-substituted $C_{1-6}$ alkyl or phenyl or unsubstituted-2-oxo-1,3-dioxoden-4-yl)methyl.

8. The penicillin derivative as defined in claim 1 wherein $R_3$ is a group for forming a pharmaceutically acceptable salt.

9. The penicillin derivative as defined in claim 1 wherein $R_3$ is $C_{1-6}$ alkyl or halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylchlorosilyl and trichlorosilyl.

10. The penicillin derivative as defined in claim 8 wherein the group for forming a pharmaceutically acceptable salt represented by $R_3$ is alkali metal atom, alkaline earth metal atom, or ammonium, or the group $COOR_3$ represents a carboxylic acid salt formed from the carboxyl group and a member selected from the group consisting of cyclohexylamine, trimethylamine, diethanolamine, arginine and lysine.

11. The penicillin derivative as defined in claim 1 wherein $R_1$ and $R_2$ are hydrogen.

12. The penicillin derivative as defined in claim 1 wherein $R_1$ and $R_2$ are $C_{1-18}$ alkyl.

13. The penicillin derivative as defined in claim 1 wherein $R_1$ and $R_2$ are mononitro-substituted benzyl.

14. The penicillin derivative as defined in claim 1 wherein $R_1$ and $R_2$ are groups for forming a pharmaceutically acceptable salt.

15. The penicillin derivative as defined in claim 14 wherein the group for forming a pharmaceutically acceptable salt represented by $R_1$ and $R_2$ is alkali metal atom, alkaline earth metal atom, or ammonium, or the groups $COOR_1$ and $COOR_2$ each represent a carboxylic acid salt formed from the carboxyl group and a member selected from the group consisting of cyclohexylamine, trimethylamine, diethanolamine, arginine and lysine.

16. A pharmaceutical composition useful for treating bacterial infections in mammals which comprises (A) a β-lactam antibiotic and (B) a compound of the formula

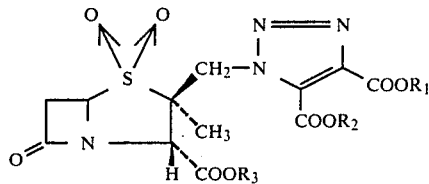

wherein $R_1$ and $R_2$ are each the same or different and represent hydrogen, $C_{1-18}$ alkyl, mononitro-substituted benzyl or group for forming a pharmaceutically acceptable salt and $R_3$ is selected from the group consisting of hydrogen, $C_{1-6}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt, the weight ratio of (A)/(B) being 0.1 to 10, said β-lactam antibiotics being selected from the group consisting of penicillins such as ampicillin, amoxicillin, hetacillin, ciclacillin, mecillinam, carbenicillin, sulbenicillin, ticarcillin, piperacillin, apalcillin, methicillin, mezlocillin, bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil and cephaloglycin; and pharmaceutically acceptable salts thereof.

17. A method of treating a bacterial infection in a mammal subject which comprises administering to said subject (A) a β-lactam antibiotic and (B) a compound of the formula

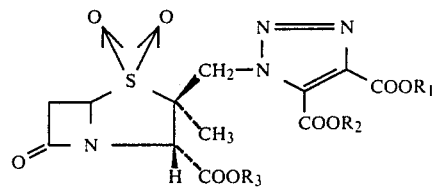

wherein $R_1$ and $R_2$ are each the same or different and represent hydrogen, $C_{1-18}$ alkyl, mononitro-substituted benzyl or group for forming a pharmaceutically acceptable salt and $R_3$ is selected from the group consisting of hydrogen, $C_{1-6}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt, the weight ratio of (A)/(B) administered being 0.1 to 10, and said β-lactam antibiotics being selected from the group consisting of penicillins such as ampicillin, amoxicillin, hetacillin, ciclacillin, mecillinam, carbenicillin, sulbenicillin, ticarbillin, piperacillin, apalcillin, methicillin, mezlocillin, bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil and cephaloglycin; and pharmaceutically acceptable salts thereof.

* * * * *